United States Patent [19]

Brandon et al.

[11] Patent Number: 5,818,719
[45] Date of Patent: Oct. 6, 1998

[54] APPARATUS FOR CONTROLLING THE REGISTRATION OF TWO CONTINUOUSLY MOVING LAYERS OF MATERIAL

[75] Inventors: Robert Griffiths Brandon; Louis Maurice Chapdelaine, both of Appleton; Leonard Michael Kaczmarzyk, Hortonville; Scott Lee Kastman, Greenville; Marci Elizabeth Kuske, Appleton; Thomas Michael Lager, Neenah, all of Wis.; Stephen Lawrence Miller, Valrico, Fla.; Robert Lee Popp, Hortonville, Wis.; Richard Thomas Wehrle, New London, Wis.; Devertt DeWayne Woolwine, Neenah, Wis.

[73] Assignee: Kimberly-Clark, Worldwide, Inc., Neenah, Wis.

[21] Appl. No.: 593,980

[22] Filed: Jan. 30, 1996

Related U.S. Application Data

[63] Continuation-in-part of Ser. No. 581,146, Dec. 29, 1995, abandoned.

[51] Int. Cl.⁶ .......................... B65H 23/00; B31B 01/88; G06F 19/00
[52] U.S. Cl. .................. 364/469.04; 226/2; 364/469.01; 364/469.03; 493/3; 493/11; 493/187; 493/381
[58] Field of Search ............................. 53/51; 226/2, 27, 226/28, 29, 32, 109; 364/400, 469.01, 469.03, 469.04, 550; 493/3, 11, 37, 186, 187, 189, 210, 264, 374, 379, 380, 381

[56] References Cited

U.S. PATENT DOCUMENTS

| | | | |
|---|---|---|---|
| 2,682,909 | 7/1954 | Claff et al. | 154/1.7 |
| 2,990,173 | 6/1961 | Melville | 270/52 |
| 3,004,880 | 10/1961 | Lord | 156/64 |
| 3,127,292 | 3/1964 | Early | 156/64 |

(List continued on next page.)

FOREIGN PATENT DOCUMENTS

| | | |
|---|---|---|
| 0 009 739 | 4/1980 | Canada . |
| 1158537 | 12/1983 | Canada . |
| 1163548 | 3/1984 | Canada . |
| 1253062 | 4/1989 | Canada . |
| 2016529 | 11/1990 | Canada . |
| 1283814 | 5/1991 | Canada . |
| 1287295 | 8/1991 | Canada . |
| 2044792 | 5/1992 | Canada . |
| 2115455 | 3/1993 | Canada . |
| 2121140 | 4/1993 | Canada . |
| 2084837 | 6/1993 | Canada . |
| 1336256 | 7/1995 | Canada . |
| 0 011 967 | 6/1980 | European Pat. Off. . |
| 0 148 115 | 7/1985 | European Pat. Off. . |
| 0 547 497 A2 | 6/1993 | European Pat. Off. . |
| 0 589 859 | 3/1994 | European Pat. Off. . |
| 0 737 638 | 10/1996 | European Pat. Off. . |
| 2 559 037 | 8/1985 | France . |
| 58-201611 | 5/1982 | Japan . |
| 635927 | 6/1986 | Japan . |

(List continued on next page.)

OTHER PUBLICATIONS

Patent Abstracts of Japan of 58–220,039: Description of Nakamura Ko et al., "Material Feeding Control System.".

*Primary Examiner*—Edward R. Cosimano
*Attorney, Agent, or Firm*—Douglas L. Miller

[57] ABSTRACT

An apparatus for controllably registering two continuously moving layers of material is provided. One of the layers of material has a plurality of reference marks representing a plurality of separate and distinct components, and the other of the continuously moving layers has a respective plurality of different components thereon. The apparatus controls the distance between reference marks to a selected distance, and controllably registers each reference mark to a respective component of the continuously moving second layer. An article is provided in which a graphic is controllably registered within a designated area thereof.

4 Claims, 8 Drawing Sheets

U.S. PATENT DOCUMENTS

| | | | |
|---|---|---|---|
| 3,276,183 | 10/1966 | Carlisle, Jr. et al. | 53/51 |
| 3,294,301 | 12/1966 | Richter | 226/27 |
| 3,326,436 | 6/1967 | Huck | 226/25 |
| 3,559,568 | 2/1971 | Stanley | 101/32 |
| 3,589,095 | 6/1971 | James et al. | 53/51 |
| 3,762,125 | 10/1973 | Prena | 53/51 |
| 3,806,390 | 4/1974 | Balk et al. | 156/229 |
| 3,811,987 | 5/1974 | Wilkinson et al. | 156/497 |
| 3,887,419 | 6/1975 | Geschwender | 156/197 |
| 3,978,637 | 9/1976 | Mauriello | 53/28 |
| 4,007,866 | 2/1977 | Traise | 226/31 |
| 4,018,028 | 4/1977 | Donnet | 53/51 |
| 4,129,238 | 12/1978 | Herd | 226/29 |
| 4,135,664 | 1/1979 | Resh | 235/475 |
| 4,239,570 | 12/1980 | Kerwin | 156/163 |
| 4,248,655 | 2/1981 | Kerwin | 156/351 |
| 4,254,173 | 3/1981 | Peer, Jr. | 428/204 |
| 4,295,912 | 10/1981 | Burns | 156/324 |
| 4,315,508 | 2/1982 | Bolick | 604/392 |
| 4,316,566 | 2/1982 | Arleth et al. | 226/2 |
| 4,322,026 | 3/1982 | Young, Jr. | 226/15 |
| 4,349,997 | 9/1982 | Hayasaka et al. | 53/51 |
| 4,392,910 | 7/1983 | Tokuno et al. | 156/361 |
| 4,397,704 | 8/1983 | Frick | 156/201 |
| 4,397,709 | 8/1983 | Schwenzer | 156/351 |
| 4,400,230 | 8/1983 | Wyslotsky | 156/361 |
| 4,417,935 | 11/1983 | Spencer | 156/80 |
| 4,496,417 | 1/1985 | Haake et al. | 156/361 |
| 4,543,141 | 9/1985 | Bradley et al. | 156/164 |
| 4,549,917 | 10/1985 | Jensen, Jr. | 156/108 |
| 4,572,752 | 2/1986 | Jensen et al. | 156/64 |
| 4,576,663 | 3/1986 | Bory | 156/64 |
| 4,610,739 | 9/1986 | Jensen | 156/64 |
| 4,615,695 | 10/1986 | Cooper | 604/385 A |
| 4,662,875 | 5/1987 | Hirotsu et al. | 604/389 |
| 4,704,171 | 11/1987 | Thompson et al. | 156/64 |
| 4,711,683 | 12/1987 | Merkatoris | 156/164 |
| 4,819,406 | 4/1989 | Redmond | 53/51 |
| 4,837,715 | 6/1989 | Ungpiyakul et al. | 364/552 |
| 4,883,549 | 11/1989 | Frost et al. | 156/161 |
| 4,888,717 | 12/1989 | Ditto et al. | 364/559 |
| 4,909,879 | 3/1990 | Ball | 156/164 |
| 4,935,087 | 6/1990 | Gilman | 156/251 |
| 4,940,464 | 7/1990 | Van Gompel et al. | 604/396 |
| 5,045,135 | 9/1991 | Meissner et al. | 156/64 |
| 5,046,272 | 9/1991 | Vogt et al. | 38/143 |
| 5,094,708 | 3/1992 | Bechtel et al. | 156/351 |
| 5,104,116 | 4/1992 | Pohjola | 271/185 |
| 5,162,066 | 11/1992 | Martensson et al. | 156/163 |
| 5,185,055 | 2/1993 | Temple et al. | 156/630 |
| 5,200,020 | 4/1993 | Collins et al. | 156/520 |
| 5,224,405 | 7/1993 | Pohjola | 83/24 |
| 5,235,515 | 8/1993 | Ungpiyakul et al. | 364/469 |
| 5,269,123 | 12/1993 | Marchesini | 53/559 |
| 5,304,272 | 4/1994 | Rohrbacker et al. | 156/209 |
| 5,359,525 | 10/1994 | Weyenberg | 364/469 |
| 5,366,791 | 11/1994 | Carr et al. | 428/195 |
| 5,389,093 | 2/1995 | Howell | 604/361 |
| 5,470,411 | 11/1995 | Gloton et al. | 156/64 |
| 5,483,893 | 1/1996 | Isaac et al. | 101/485 |
| 5,575,782 | 11/1996 | Hasse et al. | 604/385.1 |
| 5,591,152 | 1/1997 | Buell et al. | 604/385.2 |

FOREIGN PATENT DOCUMENTS

| | | |
|---|---|---|
| 2 170 486 | 8/1986 | United Kingdom . |
| 9011886 | 10/1990 | WIPO . |
| 9011887 | 10/1990 | WIPO . |
| 94/08789 | 4/1994 | WIPO . |
| WO 95/18590 A2 | 7/1995 | WIPO . |
| 97/24094 | 7/1997 | WIPO . |

APPARATUS FOR CONTROLLING THE REGISTRATION OF TWO CONTINUOUSLY MOVING LAYERS OF MATERIAL

This application is a continuation-in-part of U.S. patent application Ser. No. 08/581,146 filed Dec. 29, 1995, now abandoned.

BACKGROUND OF THE INVENTION

The present invention relates to apparatus for controlling registration, and more particularly to apparatus for controlling the registration of two continuously moving layers of material, and articles made thereby.

Various products are fabricated in a continuous production line by the sequential addition of components to previously supplied components. This is particularly advantageous when one or more of the components can be supplied in the form of a single continuous layer. For example, in the formation of disposable absorbent articles, such as training pants, diapers, incontinence articles, feminine care products, or the like, a layer is normally supplied at a point in the fabrication line in the form of a continuous roll, and absorbent pads, waist elastic bands, leg elastic bands, stretchable side panels, and/or other elements or components can be supplied at different points in the fabrication line as discrete objects.

Various methods and apparatus are available for bringing the components of a single product together so that the components in the composite product are in a desired relation with respect to each other. In bringing these components properly together, various known methods and apparatus are used to note the position of a particular component, and then to adjust the position of subsequent components in order to properly position them.

A problem encountered with these types of methods and apparatus is that they do not adequately compensate for the stretching of a continuously moving layer. During manufacturing processes of this type, a continuously moving layer is subjected to various tensions caused by it being driven or pulled through the process for handling. This tension causes the continuously moving layer to stretch, or to relax, thereby resulting in some components being undesirably positioned or, once positioned, shifted out of position. Since it is virtually impossible to maintain a constant tension on the continuously moving layer, the degree of stretching varies throughout the process. Consequently, even though an earlier positioned component may initially be within an acceptable position range, the stretching of the continuously moving layer may result in the component being outside of the acceptable position range in the final composite product.

Another problem with current methods and apparatus is that they do not provide an adequate means for registering two continuously moving layers, and particularly when one of the layers has a pre-printed or pre-positioned component or the like that is to be registered with a pre-printed or pre-positioned component or the like on the other of the layers during the manufacture of a plurality of products having a desired registration of components.

SUMMARY OF THE INVENTION

In response to the discussed difficulties and problems encountered in the prior art, an apparatus for controlling the registration of two continuously moving layers, has been discovered.

In one form of the invention, there is provided an apparatus for controllably registering a plurality of reference marks of a continuously moving first layer with a plurality of corresponding reference marks of a continuously moving second layer. The apparatus includes means for providing a continuously moving first layer including a plurality of reference marks selectively positioned thereon, means for providing a continuously moving second layer including a plurality of corresponding reference marks selectively positioned thereon, means for sensing each of the reference marks of one of the continuously moving layers and means for generating a signal in response thereto, means for measuring the distance between two reference mark signals, means for adjusting the length of the continuously moving one layer in response to the measured distance, means for super imposing the continuously moving layers together, means for detecting a reference mark of the continuously moving one layer and its corresponding reference mark of the continuously moving other layer and means for generating a signal in response thereto, and means for adjusting the speed of the continuously moving one layer in response to a generated signal in accordance with pre-programmed instructions to controllably register a reference mark of the continuously moving one layer with its corresponding reference mark on the continuously moving other layer.

BRIEF DESCRIPTION OF THE DRAWINGS

The above-mentioned and other features of the present invention and the manner of attaining them will become more apparent, and the invention itself will be better understood by reference to the following description of the invention, taken in conjunction with the accompanying drawings wherein.

DETAILED DESCRIPTION

The following detailed description will be made in the context of registering and controlling the registration of one continuously moving layer with respect to a second continuously moving layer in the manufacture of disposable absorbent articles, and specifically a child's training pant. Examples of other disposable absorbent articles include, but are not limited to, diapers, feminine care products, incontinence products, or the like. The present invention also contemplates other products or devices unrelated to disposable absorbent articles. For the purposes of this description, the term "product" can refer, but is not limited, to any article, device, laminate, composite, or the like. The term "component" can refer, but is not limited, to designated selected regions, such as edges, corners, sides or the like; structural members, such as elastic strips, absorbent pads, stretchable layers or panels, layers of material, or the like; or a graphic. The term "graphic" can refer, but is not limited, to any design, pattern, or the like.

A child's disposable training pant can have multiple appearance-related and/or functional components registered within selected machine-direction (MD) and/or cross-direction (CD) ranges. The term "machine-direction" refers to the primary direction of movement of continuously moving layers in the manufacturing process, and the term "cross-direction" refers to a direction transverse to the machine-direction. The described example herein is that of registering a graphic within a designated area of the product.

Thus, the present invention can provide a child's disposable training pant having one or more appearance-related or functional components registered with other components. Examples relating to components that are appearance-related include, but are not limited to, the registration of graphics; highlighting or emphasizing leg and waist openings in order to make product shaping more evident or visible to the user; highlighting or emphasizing areas of the product to simulate functional components such as elastic leg bands, elastic waistbands, simulated "fly openings" for boys, ruffles for girls; highlighting areas of the product to change the appearance of the size of the product; registering wetness indicators, temperature indicators, and the like in the product; registering a back label, or a front label, in the product; and registering written instructions at a desired location in the product.

Examples of functional components include, but are not limited to, waist elastics, leg elastics, areas of breathability, fluid repellent areas, fluid wettable areas, adhesives or coatings, encapsulated inks, chemically-sensitive materials, environmentally-sensitive materials, heat-sensitive materials, moisture-sensitive materials, perfumes, odor control agents, inks, fasteners, fluid storage areas, textured or embossed areas, or the like.

The training pant described herein, by way of example, comprises an absorbent pad positioned between a liquid impermeable outer cover and a liquid permeable liner. The training pant further includes elastic side panels which are joined to the outer cover in order to provide elasticity thereto. The liquid impermeable outer cover can comprise two layers of material suitably joined together, in which the innermost layer can be a liquid impermeable layer and the outermost layer can be a nonwoven layer having cloth-like texture. The innermost liquid impermeable layer has a graphic printed in registration thereon. The registered graphic generally includes a visually pleasing design or pattern and is controllably registered at a designated area in the product. One registered graphic includes a graphic positioned on the front center of the product. This graphic is preferably circular and is about 76 millimeters in dimension, and can range in size from about 25 millimeters to about 130 millimeters. The center of the graphic is about 83 millimeters from the front edge of the waist opening. The graphic may include simulated elastic leg bands, a simulated elastic waistband, a simulated "fly opening" for boys, simulated ruffles for girls, or the like.

A more detailed description of the construction and design of the above-described training pant can be found in U.S. Pat. No. 4,940,464 issued Jul. 10, 1990, the contents of which are incorporated by reference herein.

Described herein is a distinctive process and apparatus for registering a plurality of distinct and separate components on a continuously moving first layer of material with a respective plurality of distinct and separate components on a continuously moving second layer of material. The second layer of material has the components suitably represented by respective reference marks, both provided thereon at a uniform repeat length shorter than a machine product repeat length. The distance between two successive reference marks is determined and then used to calculate a desired speed for the current process conditions. The second layer of material is then controllably stretched or relaxed so that the distance between two successive reference marks substantially equals the selected distance, which in this case is one machine product repeat length; this is termed the "repeat loop". The second layer is then controllably registered to the first layer of material so that each reference mark is selectively registered with a respective component; this is termed the "placement loop". The amount of stretch or relaxation can be controllably adjusted by varying the speed and/or tension of the second layer. The term "reference mark" can refer, but is not limited, to structure such as waist or leg elastics, adhesive beads, corners or edges of structure, transporting mediums such as conveyor belts, visual marks, magnetic marks, electrical marks, electromagnetic marks, optical brighteners sensitive to ultraviolet radiation, or the like, all of which can be sensed, detected, or otherwise identified by an appropriate device. The term "machine product repeat length" refers to a selected distance, which in this example is the measured distance between successive, like components during manufacture. For example, between successive waist bands, absorbent pads, or the like. Or in other words, the machine product repeat length is the length of one product during the manufacturing process. Thus, when a reference mark is registered with a component of the first layer, then the component represented by that reference mark is registered with the component of the first layer.

With regard to the repeat loop, the second layer has the reference marks selectively provided thereon to correspond to a respective plurality of distinct and separate components, such as graphics. A first sensor generates a signal in response to each reference mark. The distance between each newly generated signal and the most recently preceding signal is suitably measured in units of a driving mechanism, so that the speed of the driving mechanism can be selectively controlled to adjust the speed and/or tension of the second layer to controllably stretch or relax the second layer, such that the distance between a subsequent newly generated signal and its most recently preceding signal is one machine product repeat length. Thus, the repeat loop refers to repeatedly duplicating a product length between two successive reference marks by accurately measuring their current distance apart and calculating a desired speed reference for a main drive control system.

With regard to the placement loop, a desired registration of a reference mark to a component is performed by comparing and controlling a related datum value to a target set point. A "datum value" refers to a measured distance between a reference mark and a machine-generated constant reference signal. A "target set point" refers to a selected value within which the datum value is maintained.

There is described herein, by way of example, a distinctive process and apparatus for using a preprinted, stretchable second layer of material including a plurality of distinct and separate graphics thereon, stretching this second layer to a selected length by varying the speed and/or tension thereof, and then applying and registering it to another layer that includes preassembled, preapplied components, such as absorbent pads, thereby providing a manufacturing process for individual disposable absorbent articles having graphics registered thereon at designated areas. The process and apparatus can also be used to apply, during manufacture, other various functional and appearance related components that have been printed, joined, positioned, or the like, on a layer at a specified location so as to be selectively registered in the final product.

The second layer of material can be a continuous polyethylene film preprinted with a plurality of separate and distinct graphics. The printed graphics are arranged such that they ultimately will be positioned at the same designated area in each finished product. The term "finished" or "final", when used with reference to a product, means that the product has been suitably manufactured for its intended purpose.

The second layer is controllably stretched or relaxed, using tension and/or speed variations, to appropriately correspond the distance between two successive reference marks to the machine product repeat length and to control a related datum value to a target setpoint. This is done in order to register the reference marks to previously processed and preplaced components, such as, by way of example, absorbent pads. The use of the term "stretchable" refers to that property of a material or composite material that permits it to recover at least a portion of its original size and shape after removal of the force causing the deformation. The stretch of the second layer is controlled by increasing or decreasing speed and/or tension using an electronically controlled, motor driven roll. Once the second layer is stretched to the desired or proper length, it may, if desired, be joined to another layer, such as a nonwoven, spunbond web to substantially stabilize the second layer, thereby reducing or eliminating its stretchability. A system of sensors used in conjunction with computer hardware and software inspects for registered location, repeat patterns, and setpoint error. The data received from these sensors is used to control the motor, which adjusts the second layers speed and/or tension as necessary for desired registration. Adjustments to the second layer are made so that the preprinted graphics are desirably registered with a respective plurality of components.

These features advantageously control a layer moving at high speed in order to register it with another layer. In particular, there is provided accurate, real time information during the production process, and rapid adjustments to the process to provide the desired configuration and registration of the reference marks and their associated components in the final product.

The use of the term "layer" can refer, but is not limited, to any type of substrate, such as a woven web, nonwoven web, films, laminates, composites, elastomeric materials, or the like. A layer can be liquid and air permeable, permeable to air but impermeable to liquids, impermeable both to air and liquid, or the like.

Each of the separate and distinct graphics on the continuously moving layer has a reference mark associated therewith. This means that each reference mark is selectively positioned with regard to a respective graphic, so that the reference mark can be sensed and appropriately registered in the product, thereby properly registering each graphic in its product. Earlier, a reference mark was described in terms of specific examples, and in the following description the reference mark is selected as an optical brightener. A reference mark, whether an optical brightener or other means, can be configured in any desired size or shape. The reference mark may comprise a generally rectangular region having a machine direction dimension of about 19 millimeters and a cross direction dimension of about 37 millimeters. Other dimensions optionally may be employed. It is to be understood that the various detecting and sensing means described herein are to be appropriately compatible with the type of associated reference mark that is to be detected or sensed. The term "associated" refers to the reference mark either being directly on a component that it represents, such as a graphic, or being selectively spaced therefrom. The optical brightener is provided to be sensitive to ultraviolet radiation. The optical brightener is, for example, capable of absorbing ultraviolet radiation and then fluorescing to emit light spectra that can be sensed by an appropriate and compatible detector or sensor. Ultraviolet radiation is generally understood to include electromagnetic radiation having wave lengths ranging from about 20–400 nanometers. Suitable optical brighteners include, for example, UVITEX OB manufactured by Ciba-Geigy, and LEUCOPURE EGM manufactured by Sandoz Chemicals Corporation.

Where the reference mark comprises ultraviolet sensitive optical brighteners, a suitable detector or sensor is a UV activated detector, such as a SICK detector model LUT 2-6 available from SICK OPTIK ELEKTRONIK, INC., a business having offices in St. Paul, Minn.

Other suitable reference marks, as well as sensors, computer devices, motors, and the like are described in U.S. Pat. No. 5,235,515; U.S. Pat. No. 5,359,525; and U.S. Pat. No. 4,837,715; the contents of these three aforementioned U.S. patents being incorporated by reference herein.

The described process and apparatus utilize several devices, and representative devices include encoders, signal counters, and sensors. An encoder generates a pulse train, which is a selected number of pulses per revolution of the encoder shaft, for subsequent counting and control. A signal counter receives a generated pulse train from an encoder, and counts the pulses for subsequent query. A sensor senses an occurrence or interruption in a process and generates a signal in response thereto.

Figure 1:
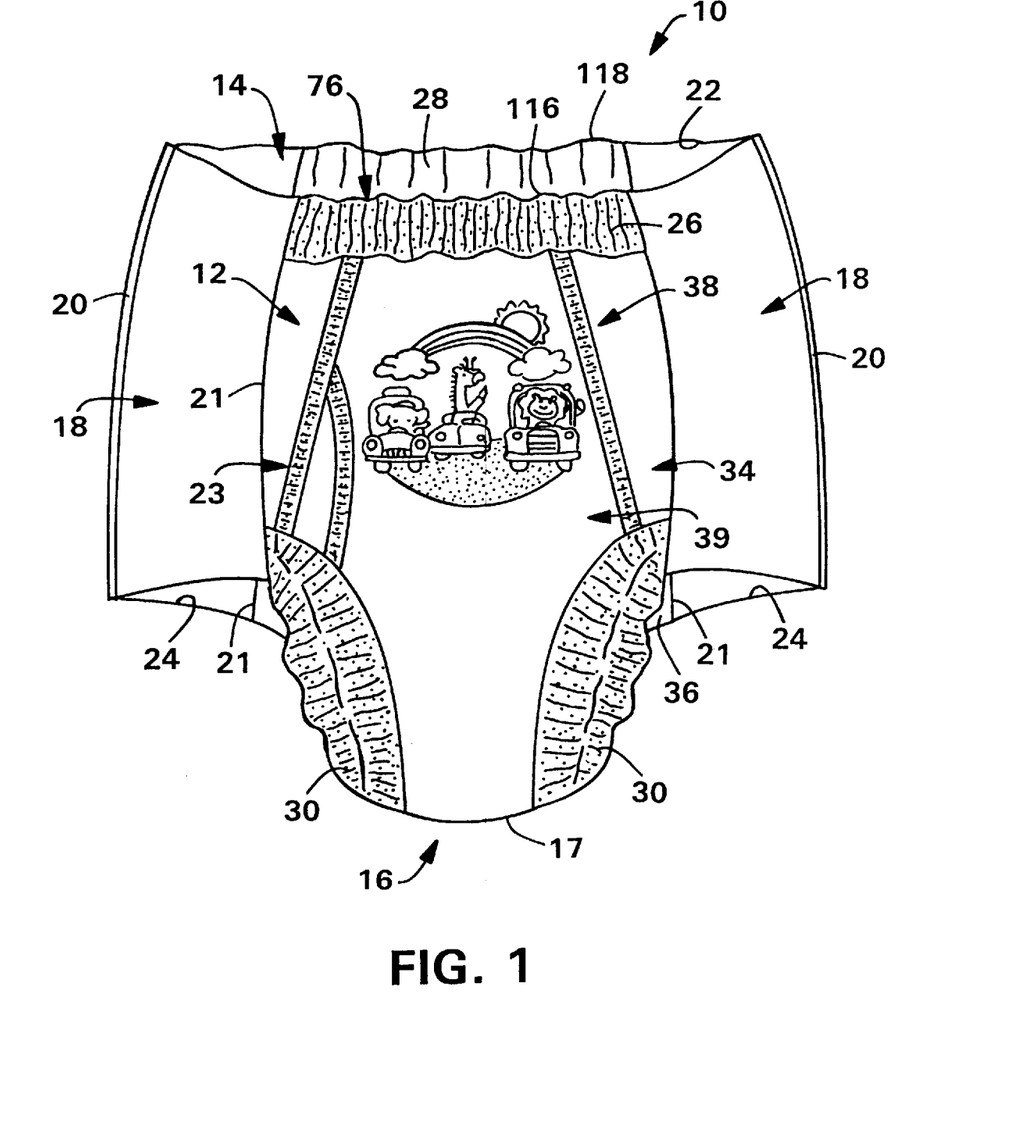
FIG. 1 illustrates a front view of one article having a registered graphic thereon.

Referring now to FIG. 1, there is illustrated a child's disposable training pant 10 generally comprising a front panel 12, a back panel 14, a crotch panel 16 interconnecting front and back panels 12, 14, and a pair of elastic side panels 18. Each elastic side panel 18 is formed from two separate elastic portions (FIG. 2A) and are suitably joined together, such as by ultrasonic bonding, to form a side seam 20. Upon the construction of side seams 20, a waist opening 22 and leg openings 24 are formed. The side seams 20 may be constructed to be manually tearable in order to allow training pant 10 to be disassembled manually by the caregiver, so that it can be easily removed from the child after a bowel movement. The elastic side panels 18 (FIG. 1) and side seams 20 can be provided in any suitable manner. One specific manner of supplying elastic side panels 18 is described in U.S. Pat. No. 5,224,405 and U.S. Pat. No. 5,104,116, both of which are incorporated by reference herein. The provision of side seams 20 can be accomplished in the manner described in U.S. Pat. No. 5,046,272, which is incorporated by reference herein.

Training pant 10 further comprises a front waist elastic 26 suitably joined to front panel 12, a back waist elastic 28 suitably joined to back panel 14, leg elastics 30 suitably joined to crotch panel 16, and an absorbent pad 32 (FIG. 4) positioned between a liquid impermeable outer cover or backsheet 34 (FIG. 1) and a liquid permeable liner or topsheet 36. The basic construction of a training pant is well known in the art, and one particular construction is that described in U.S. Pat. No. 4,940,464, issued Jul. 10, 1990, the contents of which are incorporated by reference herein. U.S. Pat. No. 4,940,464 also describes various materials of which a training pant can be made, and the methods of constructing the training pant.

As illustrated in FIG. 1, a registered graphic 38 is selectively positioned on front panel 12, and in this illustration comprises a design of a simulated "fly opening 23", typical of a boy's underwear, and a rainbow, sun, clouds, and cars. The registered graphic 38 can be any type of desired pattern, artistic feature, written instructions, or the like, and is desired to be positioned in the article at a selected location. Naturally, registered graphic 38 comprising a simulated fly opening 23 would be totally unacceptable from an aesthetic and/or functional viewpoint if it were located at crotch panel 16 or back panel 14.

Figure 2:
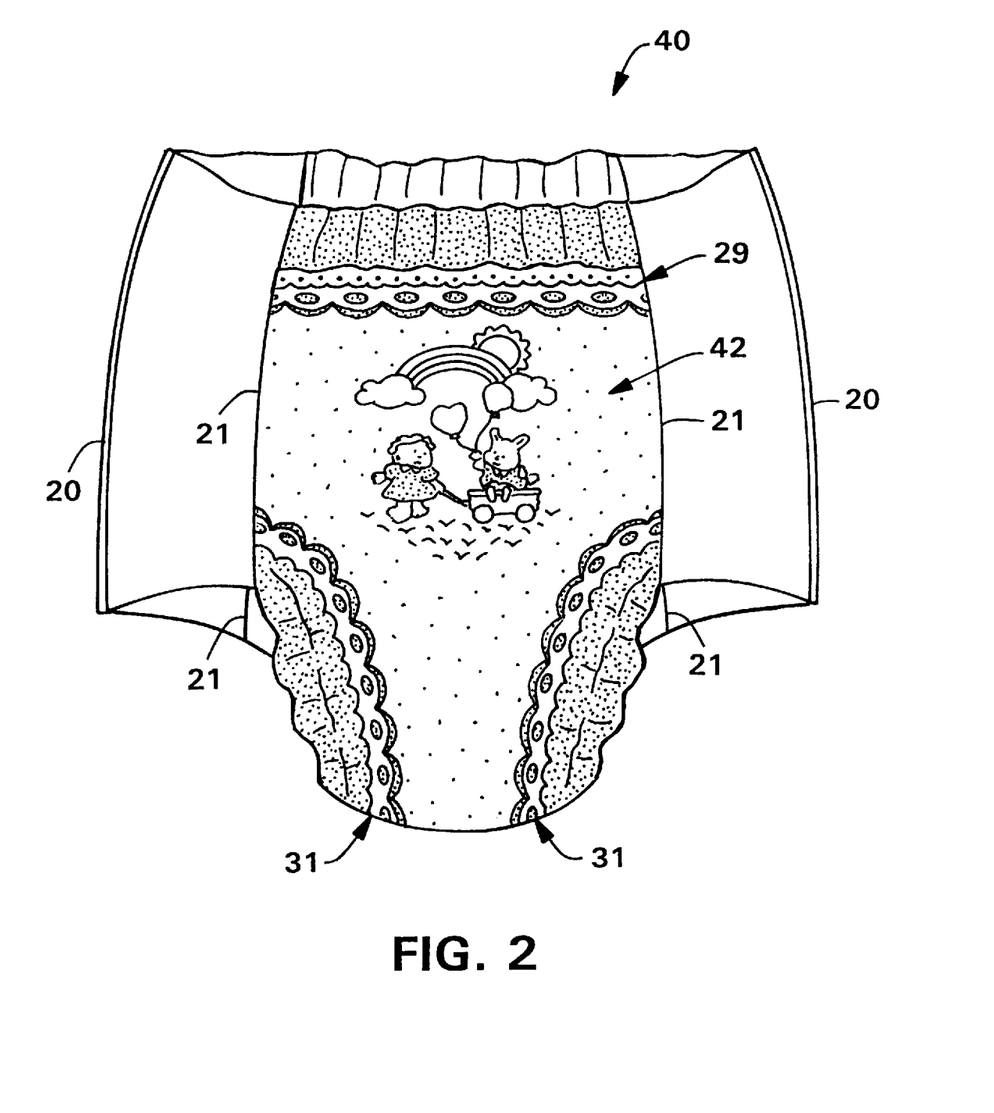
FIG. 2 illustrates a front view of another article having a registered graphic thereon.

Referring to FIG. 2, another training pant 40 is illustrated, which can be typically used for young girls. In this design, a registered graphic 42 includes simulated waist ruffles 29, simulated leg ruffles 31, a rainbow, sun, clouds, wagon and balloon. Again, any suitable design can be utilized for a training pant intended for use by young girls, so as to be aesthetically and/or functionally pleasing to them and the caregiver.

Registered graphic 38 in FIG. 1 or registered graphic 42 in FIG. 2 can be controllably registered as desired, depending upon the size and shape of the graphic and that portion of the article upon which the graphic is to be registered. In FIG. 1, graphic 38 is controllably registered within a designated area 39 which, as viewed in FIG. 1, is bounded or defined by a front waist edge 116, panel seams 21, and a crotch panel line 17. Panel seams 21 are the seams at which the respective elastic side panels 18 are suitably joined to front panel 12 and back panel 14. Again, a more specific description of the construction and manufacture of this design of a training pant 10 is contained in the aforementioned U.S. Pat. No. 4,940,464. The crotch panel line 17 is, for purposes of explanation herein, simply the line or boundary formed at the bottom of crotch panel 16 as illustrated in FIG. 1. Thus described, designated area 39 has four defined boundaries comprising front waist edge 116, panel seams 21, crotch panel line 17, and those portions of leg openings 24 extending between a respective panel seam 21 and crotch panel line 17. It is not necessary that a designated area 39 be completely defined or bounded by a closed line or closed boundary. For example, in FIG. 1, the designated area 39 could be defined by only front waist edge 116, panel seams 21, which sufficiently define a designated area 39 in which a graphic 38 can be controllably registered. In this case, the graphic 38 can be controllably registered a selected distance from front waist edge 116, and centered between panel seams 21.

Figure 2A:
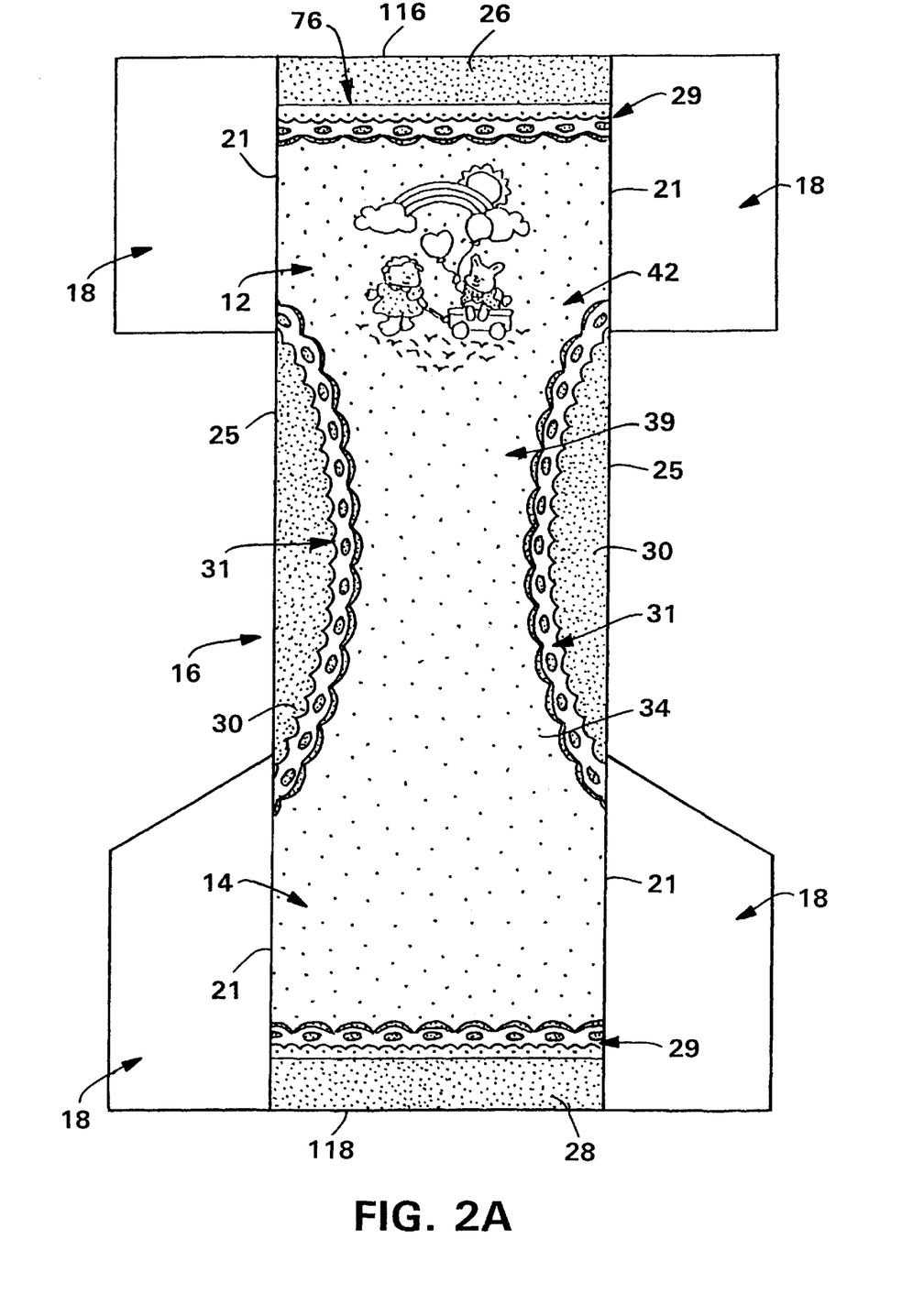
FIG. 2A representatively illustrates the article of FIG. 2 in a partially disassembled, stretched flat state.

Another example of the flexibility in choosing a designated area 39 is illustrated in FIG. 2A, which illustrates the training pant 40 in FIG. 2 in a partially disassembled, stretched flat state. This can be accomplished by taking the finished training pant 40 of FIG. 2 and manually tearing seams 20 and then laying the pant 40 flat and stretching it sufficiently to remove any gathers or pleating caused by any incorporated elastic members. In FIG. 2A, designated area 39 is defined or bounded by front waist edge 116, panel seams 21, back waist edge 118, and a pair of leg opening edges 25 extending between respective panel seams 21. Thus, in FIG. 2A, designated area 39 is generally rectangular in shape, and registered graphic 42 is registered within and throughout the surface area of designated area 39. Registered graphic 42 comprises several component designs, such as simulated leg ruffles 31 and simulated waist ruffles 29. As viewed in FIG. 2A, leg opening edges 25 are linear or straight lines. However, in FIG. 2, simulated leg ruffles 31 provide a perceived curvature or shape to training pant 40, which is one of the unique features herein.

There is uniquely and advantageously provided a very close tolerance in the registration of a desired component, such as graphics 38, 42, within any selected area, such as a designated area 39. With reference to FIG. 1, it is apparent that the simulated fly opening 23 of graphic 38 needs to be registered within front panel 12. It would be undesirable to have training pant 10 manufactured by a method and/or apparatus that could not control the proper registration of simulated fly opening 23, otherwise the simulated fly opening 23 could appear at back panel 14 or crotch panel 16. The present invention provides a highly controlled registration of a desired components, such as a graphic 38 or 42, within a desired designated area, such as designated area 39, within a tolerance of about plus or minus 6 millimeters, and within a more particular tolerance between about plus or minus 3 millimeters.

Figure 5:
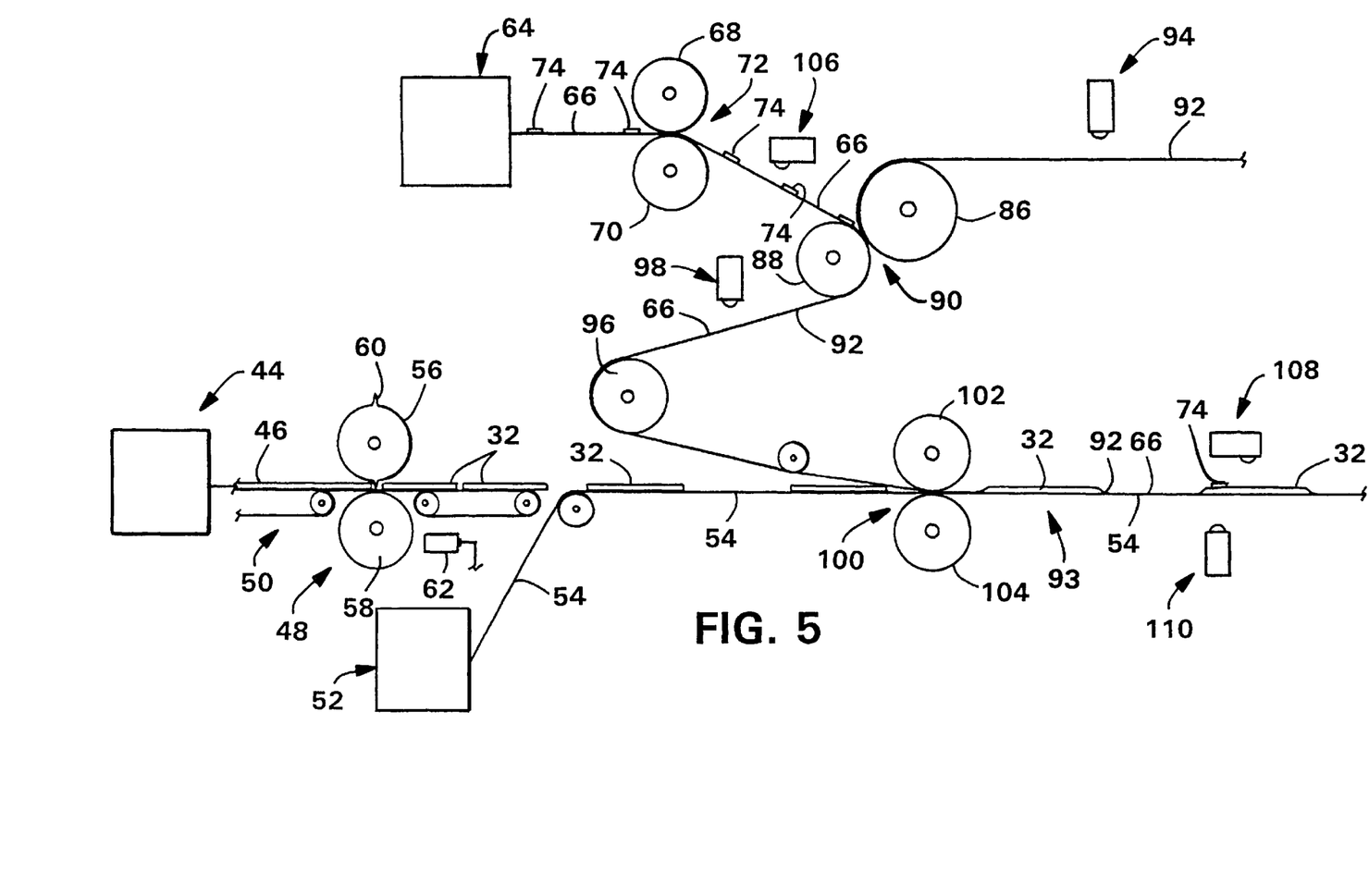
FIG. 5 schematically illustrates an apparatus and process for the manufacture of an article having a registered graphic thereon.

Referring now to FIG. 5, there is schematically shown an apparatus and process for assembling in part a plurality of training pants. A supply means 44 continuously supplies a continuous, tissue-wrapped absorbent 46 to a separating means 48 that separates the continuous, tissue-wrapped absorbent 46 into a plurality of distinct and separate absorbent pads 32. The supply means 44 can be any conventional mechanism for supplying the absorbent 46. Generally, a conventional supply means 44 will include a hammermill for forming fluff fibers and, if desired, for providing an enclosure for mixing superabsorbent material with the fluff fibers, and then depositing the fluff and superabsorbent material on a forming drum having a desired absorbent design. The forming drum then deposits the shaped absorbent on a continuously moving tissue material, which is thereafter delivered to a folding board for folding the tissue about the absorbent. This provides the continuous, tissue-wrapped absorbent 46. The absorbent can include any desired mixture or blend of absorbing materials, such as fluff and superabsorbent materials. Suitable superabsorbent materials are available from various commercial vendors such as Dow Chemical Company, Hoechst-Celanese Corporation and Allied Colloids, Inc. Typically, a superabsorbent material is capable of absorbing at least about 15 times its weight in water, and desirably more than about 25 times its weight in water. A preferred fluff is that identified with the trade designation CR1654, available from Kimberly-Clark Corporation, Neenah, Wis., and is a bleached, highly absorbent sulfate wood pulp containing primarily soft wood fibers.

A conveyor means 50, which can be any conventional conveyor means well known in the art, conveys the absorbent 46 to the separating means 48. A supply means 52 provides a continuously moving first layer of material 54, upon which can be disposed any desired component, such as the separate and distinct absorbent pads 32 formed by separating means 48. The supply means 52 can be any standard unwind mechanism that generally comprises a pair of spindles, a festoon assembly, and a dancer roll for providing first layer 54 at a desired speed and tension. One example of a standard unwind is a model MB 820, available from Martin Automatic Corporation of Rockford, Ill. The continuously moving first layer of material 54 can be any desired material suitable for the particular product being assembled. In this description of a training pant 10 (FIG. 1), continuously moving first layer 54 is a liquid permeable material that will subsequently form or become liquid permeable topsheet 36 (FIG. 1). Topsheet 36 can be made of any suitable materials well known in the art, and examples of suitable materials are described in the aforementioned incorporated U.S. patents.

Upon being moved or delivered to separating means 48, the continuous, tissue-wrapped absorbent 46 is cut into the separate and distinct absorbent pads by a knife roll 56 and an anvil roll 58 comprising separating means 48. The knife roll 56 can have any desired number of blades thereon, and in this example has two blades 60 diametrically disposed thereon for forming absorbent pads 32. Knife roll 56 is driven by and mechanically coupled through gearing to anvil roll 58, which is operatively driven by a main lineshaft 128 (FIG. 6) in any suitable manner well known in the art. A constant reference means, such as a proximity switch 62, is coupled to anvil roll 58 for generating a reference signal for each cut absorbent pad 32. For purposes herein, the separating means 48 is operated at a substantially constant speed during the manufacturing process so that each reference signal generated by proximity switch 62 is considered a machine constant reference signal for purposes of comparison to other signals hereafter described. The machine-generated constant reference signal from proximity switch 62 is transmitted to a main control system for further processing as described hereafter.

The distinct and separate absorbent pads 32 formed by separating means 48 are positioned upon the continuously moving first layer of material 54 provided by supply means 52. It is well known in the art to separate and position individually cut absorbent pads onto a continuously moving layer, and any such suitable mechanism can be utilized herein.

A supply means 64, which can be a standard unwind similar to that used with reference to the supply means 52, provides a continuously moving second layer 66 of material that will subsequently be joined to continuously moving first layer 54. The continuously moving second layer 66 can be any material suitable for the finished product, and in this particular description is a liquid impermeable film that will subsequently form liquid impermeable outer cover 34 (FIG. 1). One desired suitable liquid impermeable film is a 0.75 mil polyethylene film commercially available from Edison Plastics Company of South Plainfield, N.J. Continuously moving second layer 66 is moved toward a pair of rolls comprising a drive roll 68 and a support roll 70 that form therebetween a feed nip 72. Drive roll 68 can be driven by any suitable motor, such as those described in the U.S. patents incorporated by reference herein. A suitable feed nip motor is a HR 2000 brushless AC servo motor available from Reliance Electric Company, of Cleveland, Ohio. The material of which second layer 66 is made is desirably stretchable, in that it can be stretched, by way of example only, between about 5 to about 15 millimeters. Other materials having greater or lesser stretch can be utilized as the material or materials for second layer 66.

It is important that the feed nip motor 148 (FIG. 6) and its drive system, which operates drive roll 68, is one that is capable of performing two types of speed variations, as controlled by the main control system, which will be described in greater detail hereafter. One speed variation is to increase a present speed of the rotation to a faster speed of rotation, or to decrease a present speed of rotation to a slower speed of rotation. The other speed variation is a momentary speed variation comprising an incremental advance phase move, which is a momentary speed increase of drive roll 68 to provide a measured increased amount of the layer of material, or an incremental retard phase move, which is a momentary speed decrease of drive roll 68 to provide a measured decreased amount of the layer of material. The term "momentary speed increase" refers to increasing a first speed to a higher second speed for a selected period of time, and then causing or allowing the speed to return to the first speed, in order to advance the position of the layer and the associated graphics upstream of the nip by a measured amount. The term "momentary speed decrease" refers to decreasing a first speed to a lower second speed for a selected period of time, and then causing or allowing the speed to return to the first speed, in order to retard the position of the layer and the associated graphics upstream of the nip by a measured amount.

As described earlier, the present invention can be utilized to register two continuously moving layers together, so that a reference mark and/or product component of one layer is registered with a reference mark and/or product component on the second layer. In this particular description, a component, such as a registered graphic 38 (FIG. 1) on continuously moving second layer 66 (FIG. 5) is brought in registration with a component, such as an absorbent pad 32, on continuously moving first layer 54. By controllably registering a registered graphic 38 with an absorbent pad 32, the desired position of registered graphic 38 on a front panel 12 (FIG. 1) of a training pant 10 can be accomplished. An important function of a registered graphic 38 on a front panel 12 is that it visually informs the user of the proper orientation of the training pant 10 for donning purposes, thereby permitting the training pant to properly function, i.e., absorb waste, among other functions. The continuously moving layer 68 has, by way of example, preprinted thereon a plurality of separate and distinct graphics 38, understanding again that a graphic 38 can be any desired design or pattern, such that the graphics 38 can be registered with the separate and distinct absorbent pads 32 on continuously moving layer 54. There is associated with each graphic 38 a preprinted reference mark 74, which in this case is an optical brightener. The graphics 38 and their respective reference marks 74 can be provided on layer 66 in any suitable manner well known in the art.

Figure 3:
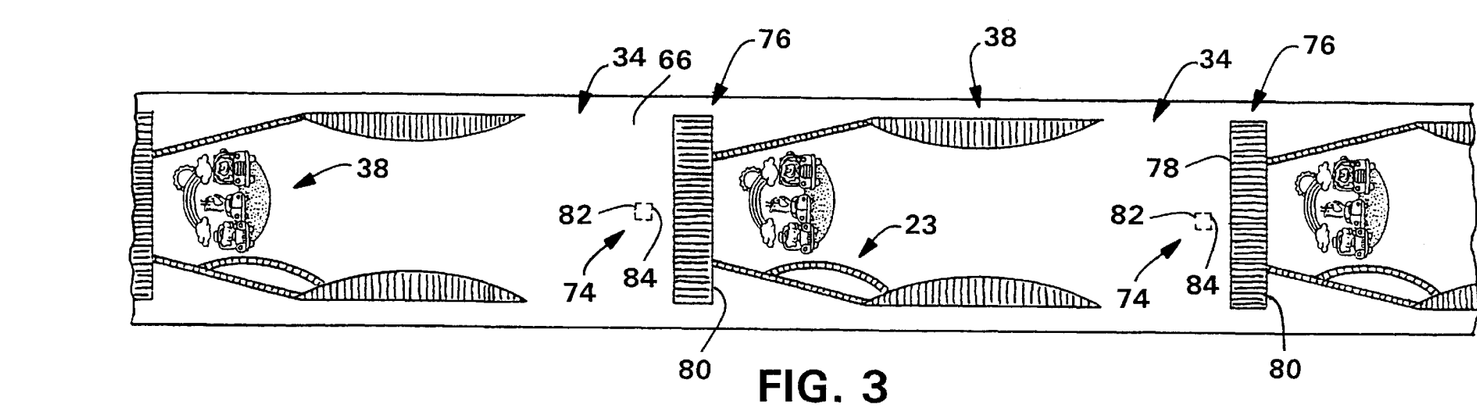
FIG. 3 illustrates a continuously moving layer having a plurality of separate and distinct graphics thereon.

With reference to FIG. 3, there is illustrated a portion of continuously moving layer 66 having a plurality of the graphics 38 and reference marks 74 preprinted or propositioned thereon. Associated with each graphic 38 is a printed waistband 76 with a printed front edge 78 and a printed back edge 80. Similarly, each reference mark 74 has a reference front edge 82 and a reference back edge 84. Each reference mark 74 will be used to properly position an associated graphic 38 with an absorbent pad 32. The reference marks 74 are positioned off graphics 38, but could be printed directly on the graphics 38 so as to be within the design of the graphics. Furthermore, the reference marks 74 can be eliminated, and a portion of a graphic 38 can be used as the reference mark. For example, a detectable mark or the like could be printed as part of the waistband 76 and thereafter used for properly registering the graphic 38. However, for purposes of explanation and manufacture, reference marks 74 are provided a selected distance apart from respective graphics 38.

In the following description, the continuously moving second layer 66 will be described, by way of example, as being joined or laminated to another third layer 92 (FIG. 5) of material in order to produce a two-layered laminate 93 that ultimately will form the liquid impermeable outer cover 34 (FIG. 1). The polyethylene film material of which layer 66 is made serves as a liquid impermeable barrier, while the third layer of material joined to layer 66 will provide cloth-like texture to the outer cover. The cloth-like layer will be the outermost layer. There is no requirement, however, for the third layer, and in some product designs, the cloth-like layer can be eliminated.

Layer 66 is driven or moved toward a laminator chill roll 86 and an associated support roll 88, which form therebetween a laminator nip 90. A continuously moving layer 92 is provided in any suitable manner, and driven in any suitable manner to laminator chill roll 86. An adhesive applicator 94 applies a desired pattern of a suitable adhesive to the continuously moving layer 92. In this particular embodiment, layer 92 is a nonwoven web, such as a spunbond polypropylene web having a basis weight of about 20 grams per square meter (gsm). The adhesive applicator 94 can be any suitable applicator well known in the art that can provide or apply the desired pattern of adhesive. The adhesive used can be any suitable adhesive that is compatible to layers 66 and 92, in order to ensure their proper lamination together. Continuously moving layer 92 can be provided by a supply means (not shown) similar to supply means 52 and 64.

Laminator chill roll 86 is driven by the lineshaft 128 (FIG. 6) and assists in moving the layers in the process. The laminator chill roll 86 also serves to cool the adhesive applied by adhesive applicator 94 for processing purposes, thereby preventing adhesives from bleeding through the layers 66 or 92.

Once layers 66, 92 are laminated and pass through laminator nip 90, they are continuously moved to a construction chill roll 96, and have an adhesive applied to the outermost surface of layer 66. Construction chill roll 96 is lineshaft driven by lineshaft 128, similar to chill roll 86. The adhesive applied by adhesive applicator 98 will ultimately join layers 66, 92 to continuously moving first layer 54. Thus, the adhesive applicator 98 is selected to apply the appropriate adhesive pattern and amount of adhesive to ensure the desired joining of the layers 66, 92, and 54. The construction adhesive applicator 98, as well as the adhesive applied thereby, can be any type of applicator suitable for the desired adhesive pattern, and appropriate and compatible for the materials to be joined.

From construction chill roll 96, the laminated layers 66, 92 are then superimposed over continuously moving layer 54, and together the layers pass through a product tacker 100 comprising a drive roll 102 driven by lineshaft 128 (FIG. 6) and a rubber-coated idler roll 104. Tacker 100 compresses the layers together in order to cause the applied adhesive to join layers 66, 92 to continuously moving layer 54, thereby forming a continuously moving composite laminate 93 as illustrated in FIG. 4.

Continuing to refer to FIG. 5, a first sensing means, such as a sensor 106, is suitably positioned between drive roll 68 and laminator chill roll 86 for detecting and generating a signal in response to each reference mark 74. Since the reference marks 74 are ultraviolet-sensitive optical brighteners, a suitable sensor is a SICK detector model LUT 2-6 available from SICK OPTIK ELEKTRONIK, Inc., having a business office in St. Paul, Minn.

Positioned downstream of product tacker 100 are a second and third sensing means, such as a sensor 108 and a photoeye 110. The term "downstream" refers to a left-to-right direction as viewed in FIG. 5, and is also the machine direction for the process. Parenthetically, although layers 66 and 92 are illustrated as moving in a downwardly direction, the primary direction in which they are moving or will eventually move is in a left-to-right direction, and is also thus termed the downstream direction. Sensor 108 can be the same type of ultraviolet detector as sensor 106. The photoeye 110 is desirably a Banner RSBF scanner block, RPBT wiring base, IR 2.53S fiber-optic pair device, available from Banner Engineering, Corp. of Minneapolis, Minn. Photoeye 110 is designed to optically detect a product component, such as absorbent pad 32, and to generate an electrical signal in response thereto. In this particular description, both sensors 106 and 108 are designed to detect and generate a signal in response to a reference mark 74, and photoeye 110 is designed to detect and generate a signal in response to an absorbent pad 32. If desired, photoeye 110 can sense other components, such as waist elastics, leg elastics, fastening tapes utilized in diapers, or the like. A reference mark also can be associated with each absorbent pad 32 in the same manner that a reference mark 74 is associated with a graphic 38; and in that case, the pad photoeye 110 can be replaced with a sensor similar to sensors 106, 108. Similarly, sensors 106, 108 can be replaced with other sensors, similar to photoeye 110, in order to optically detect a product component or other structure in order to generate an appropriate signal.

Figure 4:
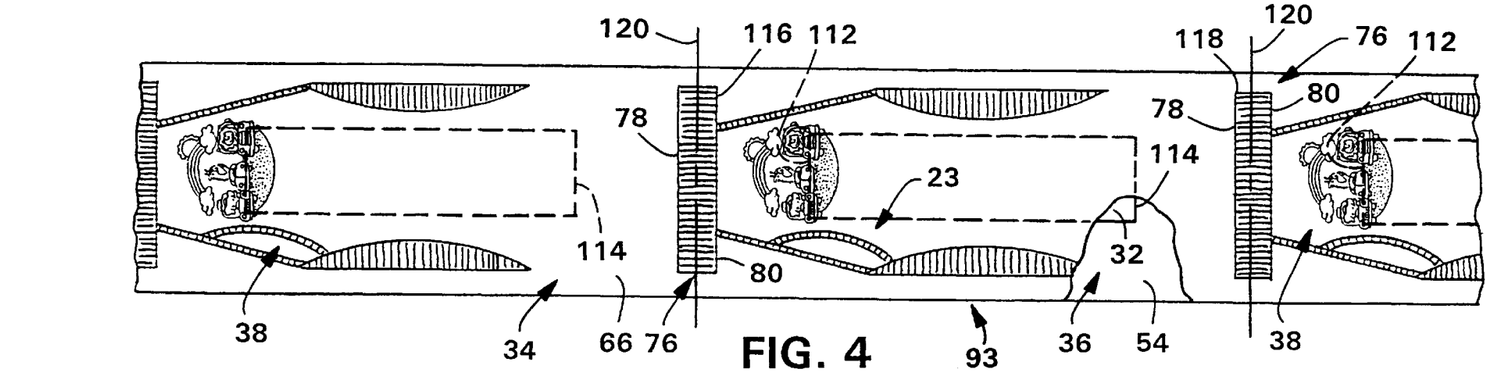
FIG. 4 illustrates a continuously moving composite layer having a plurality of separate and distinct graphics thereon.

With reference to FIG. 4 and FIG. 5, there is illustrated a continuously moving composite laminate 93 comprising layers 66, 92, and 54 after they have been joined together by product tacker 100. Each printed waistband 76 will ultimately be cut along a respective cut line 120 in order to form individual products. In FIG. 4, once cut lines 120 have been separated, a front waist edge 116 and a back waist edge 118 are formed for each assembled product. Each absorbent pad 32 includes a front edge 112 and a back edge 114. One of the important features in FIG. 4 is the relative placement of a graphic 38 with respect to each product that will eventually be formed. Each graphic 38 is located in the front panel 12 (FIG. 1) and is located in the same position relative to an absorbent pad front edge 112 (FIG. 4). Naturally, other marks or product components can be in registration with other different reference marks or product components. For example, a simulated waist ruffle 29 (FIG. 2) can be registered relative to a waist opening, or leg elastics, such as leg elastics 30 (FIG. 1), can be desirably registered in relation to an absorbent pad, such as absorbent pad 32 (FIG. 4).

Figure 6:
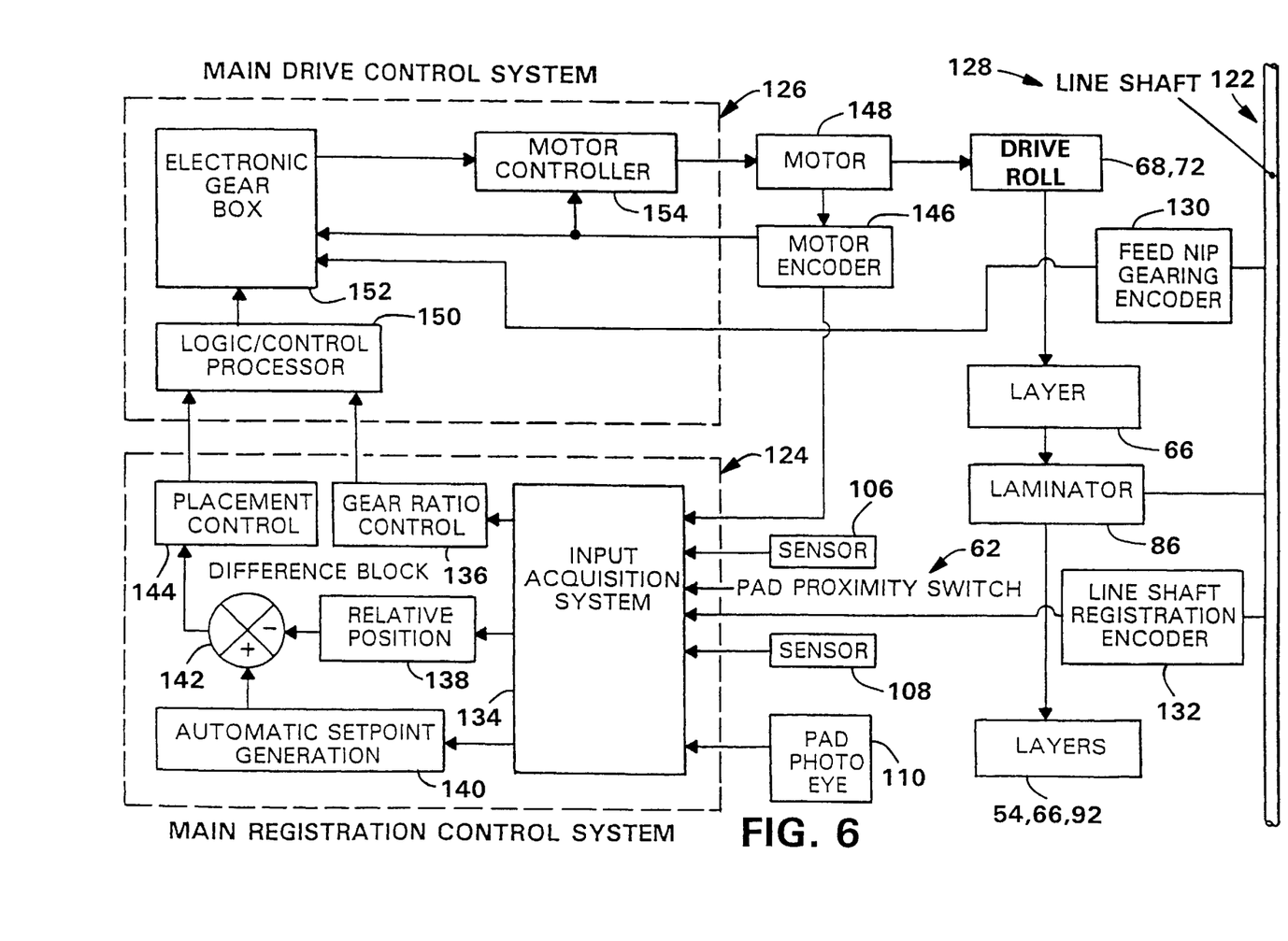
FIG. 6 illustrates a schematic block diagram of the flow of data utilized in conjunction with the apparatus and process in FIG. 5.

Referring to FIG. 6, there is schematically illustrated a main control system with the mechanical side 122. The main control system comprises a main registration control system 124 that receives various generated signals, processes them in accordance with programmed instructions, and generates output signals to a main drive control system 126. The main drive control system 126 receives the signals from the main registration control system 124, and in response thereto operatively adjusts drive roll 68 (FIG. 5).

Mechanical side 122 comprises a lineshaft 128 that directly drives selected mechanisms or, through a system of gears and other coupling devices, both electrical and mechanical, indirectly drives other mechanisms. Lineshaft 128 is driven at a constant speed, by any suitable means known in the art. Thus, those mechanisms driven by lineshaft 128 are also driven at a constant speed, which may or may not be the same speed as that of lineshaft 128. Specifically, a feed nip gearing encoder 130 and a lineshaft registration encoder 132 are operatively coupled to lineshaft 128. Examples of encoders include an H25D-SS-2500-ABZC-8830-LED-SM18 (which can be used as encoder 130), available from BEI Motor System, Co. of Carlsbad, Calif., and a 63-P-MEF-1000-T-0-00 (which can be encoder 132) available from Dynapar Corp. of Gurnee, Ill. Feed nip gearing encoder 130 is operatively coupled to lineshaft 128 to rotate at a constant speed, and such that four revolutions of encoder 130 represents one machine-generated product length, i.e, a machine product repear length.

The main registration control system 124 comprises hardware and/or preprogrammed software instructions, and can be represented, with reference to FIG. 6, as comprising an input acquisition system 134, a gear ratio control 136, a relative position 138, an automatic set point generation 140, a difference block 142, and a placement control 144. The main registration control system 124 includes a computer, which can comprise, for example, a VME-based microprocessor, such as a SYS68K/CPU-40B/4-01 available from Force Computers, Inc. of Campbell, Calif.

As illustrated in FIG. 5 and FIG. 6, input acquisition system 134 receives the following six generated signals: (i) a signal from a motor encoder 146 operatively coupled to the feed nip motor 148, (ii) a signal from sensor 106 (FIG. 5), (iii) a signal from proximity switch 62, (iv) a signal from lineshaft registration encoder 132, (v) a signal from sensor 108, and (vi) a signal from photoeye 110. Input acquisition system 134 receives and counts the pulses generated by motor encoder 146 and lineshaft registration encoder 132, and receives signals from sensors 106, 108, proximity switch 62, and photoeye 110. Referencing the accumulated counts of encoder 146 and the accumulated counts of encoder 132, input acquisition system 134 performs preprogrammed instructions that are specific to the respective received signals, and stores the results of the instructions.

The input acquisition system 134 performs the following functions for the gear ratio control 136. A signal counter in input acquisition system 134 counts the pulses from motor encoder 146, and receives signals from sensor 106 in response to each reference mark 74 (FIG. 5). The input acquisition system 134 then measures the counted pulses representing a distance between every two successive reference marks 74, and performs a running average of those measured counts. The term "running average" refers to averaging the same number of data; for example, for each newly received datum input, the latest, i.e. the oldest, datum is removed from the averaging calculation. The averaging of the counts between two successive reference marks 74 creates an average measurement upon which the next gear ratio value will be derived by gear ratio control 136, as opposed to basing a control decision on the measurement from just one pair of reference marks 74. This averaging "smooths out" the measurements, and is necessitated due to the variability of the apparatus and process. The number of measurements to average is controllable, and is set or determined by providing an appropriate instruction via manual input in any suitable manner well known in the art. In conjunction with performing a running average of the measured counts, the input acquisition system 134 performs a filtering function, which is preprogrammed, to filter out signal anomalies. Examples of such signal anomalies include a dirty photoeye, missing or extra reference marks 74, movement or weaving of the layers, measuring the counts outside a preprogrammed range for averaging purposes, known inaccurate data due to registration control events, or the like.

The input acquisition system 134 performs the following functions for the relative position 138. The input acquisition system 134 counts the pulses received from lineshaft registration encoder 132, and receives signals generated by sensor 106 and proximity switch 62. Input acquisition system 134 then determines and records the current accumulated number of pulses upon receiving a signal from sensor 106, and determines and records the current accumulated number of pulses upon receiving a signal from proximity switch 62.

The input acquisition system 134 performs the following functions for the automatic set point generation 140. Input acquisition system 134 counts the pulses received from lineshaft registration encoder 132, and receives the signals generated by sensor 108 and photoeye 110. It then determines and records the current accumulated number of pulses upon receiving a signal from sensor 108, and determines and records the current accumulated number of pulses upon receiving a signal from photoeye 110. Thereafter, input acquisition system 134 calculates the difference between the current accumulated number of pulses from one signal of sensor 108 and the current accumulated number of pulses from an associated signal of photoeye 110; the "associated signal" refers to the signal generated by photoeye 110 (FIG. 5), with the signal from sensor 108, for each machine product repeat length. With these calculated differences, input acquisition system 134 performs a running average and standard deviation for those differences.

The various calculations and functions performed by input acquisition system 134 are utilized by other portions of main registration control system 124 in order to generate commands to main drive control system 126 (FIG. 6). Main drive control system 126 generally comprises a logic/control processor 150, an electronic gear box 152, and a motor controller 154. The main drive control system 126 includes a computer, which can comprise, for example, a Reliance Distributed Control System made by Reliance Electric, Co. The Distributed Control System includes a Reliance Electric Automax Processor and associated hardware. The electronic gear box 152 (FIGS. 6–7) comprises a 2-axis card that is part of the Distributed Control System unit and is used to control the position of motor 148.

Within main registration control system 124, the gear ratio control 136 queries the input acquisition system 134 every 20 products, i.e., every 20 machine product repeat lengths, for the current running average of measured counts representing a distance between successive reference marks 74 (FIG. 5), which is the repeat value. The number of product lengths determining a query from gear ratio control 136 is adjustable, and can be changed manually by the operator. After determining the repeat value, gear ratio control 136 performs a gear ratio calculation in accordance with preprogrammed instructions to determine a new gear ratio value. That new gear ratio value is then transmitted to the logic/control processor 150 of main drive control system 126. The gear ratio value is calculated by dividing the repeat value by the number of encoder counts from the feed nip gearing encoder 130 (FIG. 6) that occur in one machine product repeat length. The advantage of this is the ability to controllably regulate the repeat of reference marks without comparing to a target value, and the ability to rapidly compensate for processing irregularities and changes in the layer of material that can alter the desired repeat of reference marks.

The relative position 138 of main registration control system 124 queries input acquisition system 134 for the current accumulated number of pulses relative to sensor 106, and the current accumulated number of pulses relative to proximity switch 62. Relative position 138 then determines the difference between the two current accumulated number of pulses in order to calculate a relative position of a reference mark 74 (FIG. 5) to the associated proximity switch signal for that specific query for each machine product repeat length. The relative position 138 then generates and transmits to difference block 142 a relative position value.

The automatic set point generation 140 queries the input acquisition system 134 for each machine product repeat length representing a single product. The occurrence of each product, or machine product repeat length, is determined from the lineshaft registration encoder 132, in which two revolutions of lineshaft registration encoder 132 is equivalent to one product length. In this particular example, two revolutions of lineshaft registration encoder 132 is 2,000 counts. The input acquisition system 134 responds to each query from automatic set point generation 140 with the current running average and standard deviation of the difference calculated between the current accumulated number of pulses for one signal of sensor 108 and the current accumulated number of pulses from an associated signal from pad photoeye 110 for each product; the current running average of this calculation is the actual position value. The automatic set point generation 140 then compares a standard deviation with a preset limit, which has been manually entered, and if the standard deviation is outside the preset limit, the automatic set point generation 140 will ignore that datum and not determine a new set point since the standard deviation data is considered too variable to make an accurate set point adjustment. If the standard deviation is within the preset limit, the automatic set point generation 140 will then determine the difference between the actual position value and a manually entered target value, which is the desired actual position value. If the new calculated difference is determined, by automatic set point generation 140, to be within a prescribed range, no further action or calculation will be made. However, if the difference is outside the prescribed range, the automatic set point generation 140 will determine a new control set point. This new control set point is derived by adding to the current set point the difference between the target value and actual position value.

Referring now to FIG. 6, once every machine product repeat length, a difference block 142 determines the difference between the current control set point value from automatic set point generation 140 and the associated relative position value from relative position 138, which is the placement error. The difference block 142 transmits this placement error, in lineshaft encoder counts, to placement control 144. The placement control 144 compares the placement error to a tolerance band 170 (FIG. 8), which defines an acceptable deviation of the relative position value about the current control set point. The tolerance band 170 remains constant about the control set point, but the control set point can vary as calculated by automatic set point generation 140. As a result, while the position control of the reference marks occurs at the nip, the setpoint for this position control is accurately derived from the signals generated by sensor 108 and photoeye 110.

Figure 8:
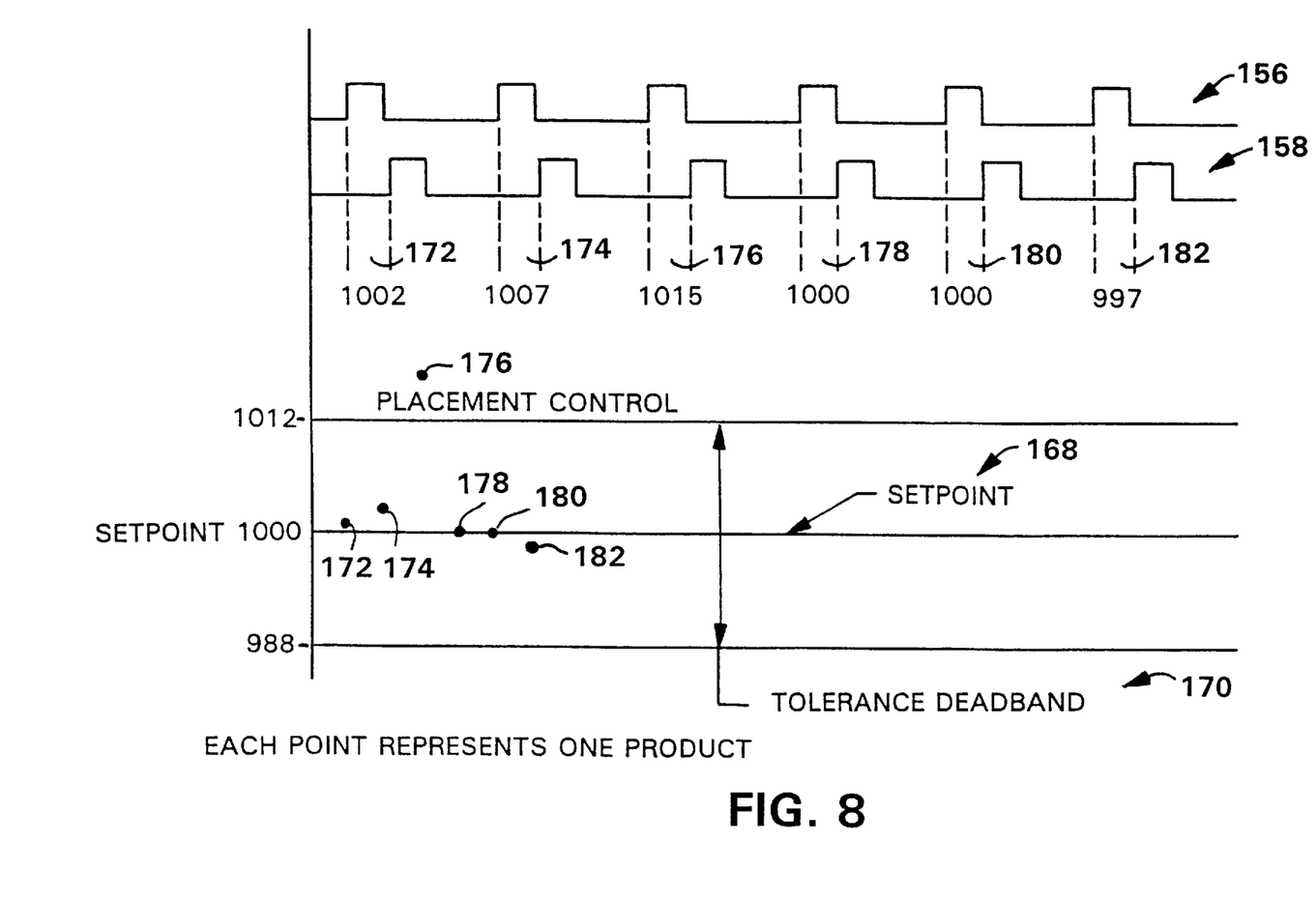
FIG. 8 graphically illustrates a placement control utilized in conjunction with the apparatus and process in FIG. 5.

With reference to FIG. 8, there is illustrated one derived set point 168 having a prescribed tolerance band 170. For purposes of explanation, the control set point 168 has a value of 1,000 counts, and the tolerance band 170 represents a deviation of plus or minus 12 counts. Each of the datum points 172, 174, 176, 178, 180 and 182, represents one product's relative position value as calculated by relative position 138. Waveform 156 represents signals generated by proximity switch 62, and waveform 158 represents signals generated by sensor 106. If a placement error value remains within tolerance band 170, no placement command will be generated. However, if a placement error value is outside tolerance band 170, then placement control 144 will generate a placement command. The placement command is directly proportional to the size of the difference represented by the value from difference block 142 and calls for a measured advance or retard in the position of layer 66. The generated placement command is then transmitted to the logic/control processor 150 of main drive control system 126. FIG. 8 illustrates an example of how placement control 144 (FIG. 6) compares each datum point 172–182 to a current control set point in order to generate a placement error. The placement error for each datum point is compared to tolerance band 170 to determine if a placement command should be generated. In the example, point 176 is the only datum point where the placement error falls outside the tolerance band 170, which causes a placement command to be generated, thereby causing a following datum point to fall within the tolerance band 170.

Figure 7:
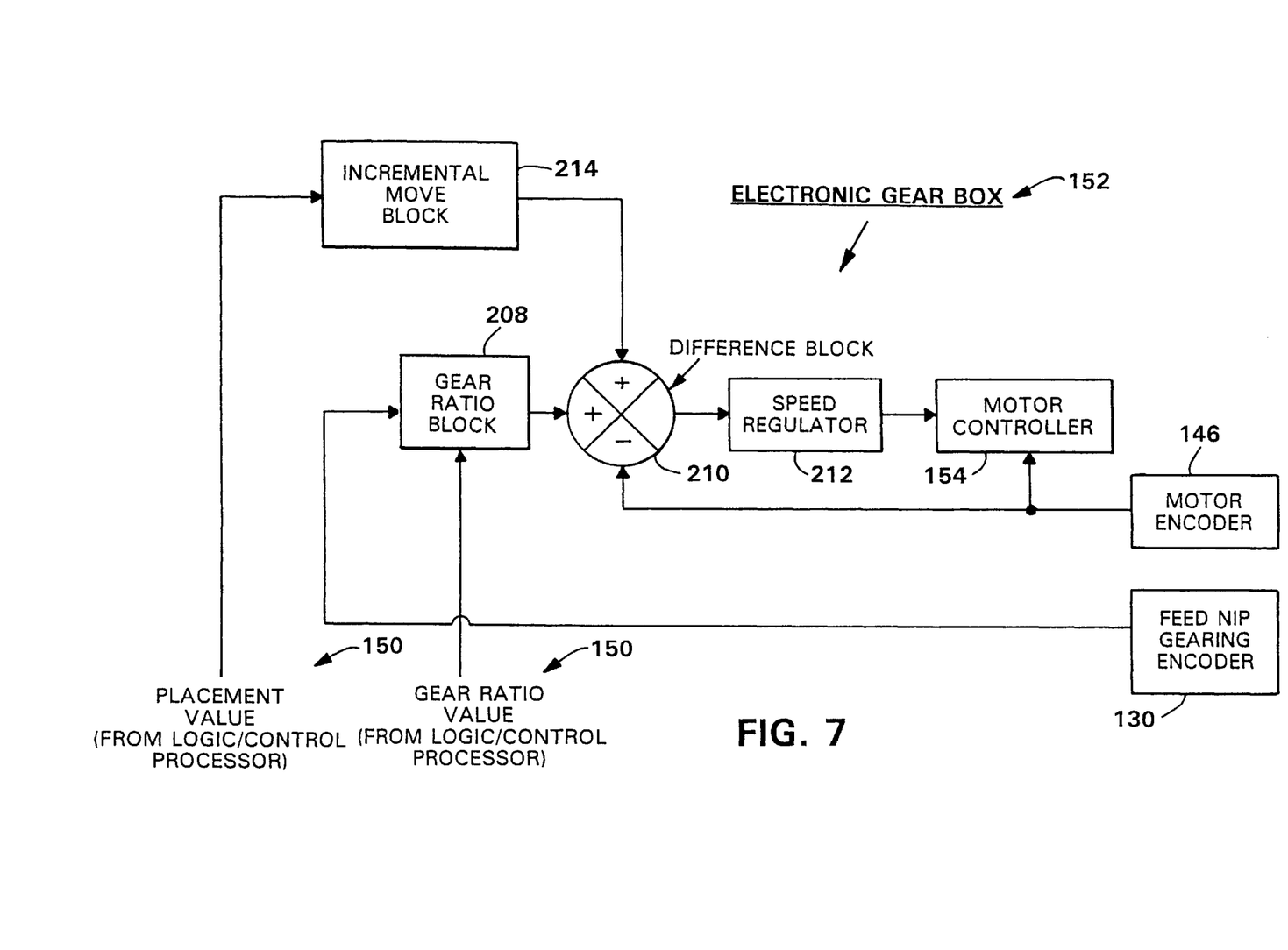
FIG. 7 illustrates a block diagram of the electronic gear box in FIG. 6.

The logic/control processor 150 (FIGS. 6 and 7) searches for and receives new commands from main registration control system 124. Specifically, processor 150 searches for and receives gear ratio commands from gear ratio control 136, and placement commands from placement control 144. For each gear ratio value update command, processor 150 transmits a command in accordance with preprogrammed instructions to electronic gear box 152 to modify the value used in a gear ratio block 208 (FIG. 7). For each placement command received from placement control 144, processor 150 transmits a placement command in accordance with preprogrammed instructions to electronic gear box 152.

Referring to FIGS. 7 and 8, electronic gear box 152 is schematically illustrated as comprising a gear ratio block 208, a difference block 210, a speed regulator 212, and an incremental move block 214. The gear ratio block 208 receives a gear ratio value from logic/control processor 150 (FIG. 6), and receives a pulse train from the feed nip gearing encoder 130. Gear ratio block 208 scales the pulse train from gearing encoder 130 and applies the gear ratio value to it in order to generate a reference signal to difference block 210. Difference block 210 receives both the reference signal from gear ratio block 208, and also receives a feed back signal from motor encoder 146, which communicates the current speed of motor 148. The difference block 210 determines the difference between the signals and generates a command signal to a speed regulator 212, which generates a speed reference signal to motor controller 154. Thus, the electronic gear box 152 precisely links the speed of the poly nip drive motor 148 to the speed of the lineshaft 128 through an electronically changeable gear ratio. This effectively synchronizes the speed of the nip motor 148 to the lineshaft 128 and allows frequent changes to the gear ratio, and thus the speed of motor 148.

With reference to FIGS. 6–7, electronic gear box 152 also receives a placement value from logic/control processor 150, and this placement value is received by incremental move block 214. Incremental move block 214 performs a "one time" move to appropriately change the reference signal by a measured amount of poly nip motor encoder counts, thereby calculating an exact one time increase or decrease in the amount of the layer of material being supplied by the nip motor 148. This can be done by relating the number of encoder counts of the motor encoder 146 to an actual amount of the layer of material supplied at the nip 72 (FIG. 5). In response to the placement command, an incremental move signal is generated and temporarily added to difference block 210, which increments or decrements, the reference signal received from gear ratio block 208, thereby resulting in a momentary change in the speed command signal sent to the speed regulator 212. Motor controller 154 receives the speed command signal from electronic gear box 152 (FIG. 6) and varies the speed of motor 148, which is represented by the motor encoder pulse train, in response thereto.

As described, the desired registration of graphic 38 (FIG. 1) or graphic 42 (FIG. 2) in respective training pants 10, 40 can be accomplished. By selectively controlling the distance between successive reference marks 74 (FIG. 5), each mark 74 can be desirably registered with an associated component, such as an absorbent pad 32. Controlling the distance between reference marks 74 to a selected distance, such as machine product repeat length, accommodates or corrects for variations or other types of anomalies that may be present in the apparatus or process. By adjusting the speed and/or tension of continuously moving second layer 66, it can be appropriately registered with continuously moving first layer 54, thereby ensuring proper registration of a desired component, such as a graphic 38, to another component, such as a front panel 12 (FIG. 1).

While this invention has been described as having a preferred embodiment, it will be understood that it is capable of further modifications. It is therefore intended to cover any variations, equivalents, uses, or adaptations of the invention following the general principles thereof, and including such departures from the present disclosure as come or may come within known or customary practice in the art to which this invention pertains and fall within the limits of the appended claims.

What is claimed is:

1. An apparatus for controllably registering a plurality of reference marks of a continuously moving first layer with a plurality of corresponding reference marks of a continuously moving second layer, comprising:

means for providing a continuously moving first layer including a plurality of reference marks selectively positioned thereon, means for providing a continuously moving second layer including a plurality of corresponding reference marks selectively positioned thereon, means for sensing each of the reference marks of one of the continuously moving layers and means for generating a signal in response thereto, means for measuring the distance between two reference mark signals, means for adjusting the length of the continuously moving one layer in response to the measured distance, means for superimposing the continuously moving layers together, means for detecting a reference mark of the continuously moving one layer and its corresponding reference mark of the continuously moving other layer, and means for generating a signal in response thereto, and means for adjusting the speed of the continuously moving one layer in response to a generated signal in accordance with preprogrammed instructions to controllably register a reference mark of the continuously moving one layer with its corresponding reference mark on the continuously moving other layer.

2. The apparatus of claim 1 wherein the reference marks of the one layer are spaced apart a selected distance, and wherein the reference marks of the second layer are spaced apart a different selected distance.

3. The apparatus of claim 2 wherein the reference marks of the one layer are spaced apart a distance less than a machine product repeat length.

4. The apparatus of claim 3 wherein the reference marks of the other layer are spaced apart a distance substantially the same as a machine product repeat length.

\* \* \* \* \*